(12) United States Patent
Enenkel

(10) Patent No.: US 10,420,492 B2
(45) Date of Patent: Sep. 24, 2019

(54) BIOMETRIC SENSOR ARRANGEMENT AND METHOD FOR GENERATING A BIOMETRIC SIGNAL

(71) Applicant: ams AG, Unterpremstaetten (AT)

(72) Inventor: Jan Enenkel, Gratkorn (AT)

(73) Assignee: ams AG, Unterpremstaetten (AT)

( * ) Notice: Subject to any disclaimer, the term of this patent is extended or adjusted under 35 U.S.C. 154(b) by 515 days.

(21) Appl. No.: 15/221,448

(22) Filed: Jul. 27, 2016

(65) Prior Publication Data

US 2017/0027488 A1 Feb. 2, 2017

(30) Foreign Application Priority Data

Jul. 28, 2015 (EP) .................................... 15178625

(51) Int. Cl.
*A61B 5/1455* (2006.01)
*A61B 5/00* (2006.01)
*A61B 5/024* (2006.01)
*A61B 10/00* (2006.01)

(52) U.S. Cl.
CPC ...... *A61B 5/14552* (2013.01); *A61B 5/02416* (2013.01); *A61B 5/443* (2013.01); *A61B 5/4872* (2013.01); *A61B 5/4875* (2013.01); *A61B 5/681* (2013.01); *A61B 5/6898* (2013.01); *A61B 2010/0009* (2013.01); *A61B 2562/0233* (2013.01); *A61B 2562/0238* (2013.01)

(58) Field of Classification Search
CPC ... A61B 5/145; A61B 5/02416; A61B 5/4875; A61B 5/443; A61B 5/6898; A61B 5/681; A61B 5/4872; A61B 2562/0233; A61B 2562/0238; A61B 2010/0009

See application file for complete search history.

(56) References Cited

U.S. PATENT DOCUMENTS

| 8,954,135 | B2 | 2/2015 | Yuen et al. | |
|---|---|---|---|---|
| 9,433,057 | B1 * | 8/2016 | Janning | ............... H05B 33/0821 |
| 2005/0075553 | A1 | 4/2005 | Sakai et al. | |
| 2005/0119543 | A1 * | 6/2005 | Parker | ................ A61B 5/14532 600/323 |

(Continued)

FOREIGN PATENT DOCUMENTS

| DE | 102011104975 A1 * | 12/2012 |
|---|---|---|
| EP | 2502554 A1 | 9/2012 |

OTHER PUBLICATIONS

"AFE4400 Integrated Analog Front-End for Heart Rate Monitors and Low-Cost Pulse Oximeters", Texas Instruments; SBAS601H, Dec. 2012, revised Jul. 2014, 87 pages.

(Continued)

*Primary Examiner* — Eric F Winakur
*Assistant Examiner* — Abid A Mustansir
(74) *Attorney, Agent, or Firm* — Fish & Richardson P.C.

(57) ABSTRACT

A biometric sensor arrangement (10) comprises a first radiation source (11), a second radiation source (12) that is implemented as a flash radiation source and a driver (13) coupled to the first and the second radiation source (11, 12) and configured to selectively operate the first and the second radiation source (11, 12). Moreover, the biometric sensor arrangement (10) comprises a photosensor (16) and a signal conditioning unit (18) coupled to the photosensor (16) and designed to provide a biometric signal (SB).

16 Claims, 11 Drawing Sheets

(56) References Cited

U.S. PATENT DOCUMENTS

| | | | |
|---|---|---|---|
| 2006/0267040 A1* | 11/2006 | Baek | H01L 25/167 |
| | | | 257/99 |
| 2007/0282183 A1* | 12/2007 | Scholler | A61B 5/14551 |
| | | | 600/328 |
| 2013/0272688 A1 | 10/2013 | Trattler et al. | |
| 2014/0213863 A1 | 7/2014 | Loseu et al. | |
| 2014/0221854 A1 | 8/2014 | Wai | |
| 2015/0133756 A1 | 5/2015 | Petersen et al. | |
| 2015/0190094 A1 | 7/2015 | Lee et al. | |
| 2015/0196239 A1 | 7/2015 | Meehan et al. | |
| 2016/0081602 A1* | 3/2016 | Lisogurki | A61B 5/14551 |
| | | | 600/476 |

OTHER PUBLICATIONS

AMS Product "TMG 3992", ams Datasheet, Oct. 24, 2014, 95 pages.

"Performance-Level Continuous Heart Rate Technology", retrieved from <http://www.mioglobal.com/en-uk/mio-heart-rate-technology.htm> on Feb. 26, 2015, 4 pages.

Osram Product, "BPW 34 / BPW 34 S", Datasheet, Mar. 10, 2004, 6 pages.

Samsung Galaxy S5, "Capturing Lifetime Moments", Datasheet retrieved on Feb. 26, 2015, 17 pages.

TAOS Product, "TSL12S, TSL13S, TSL14S", Datasheet TAOS051E, Sep. 2007, 13 pages.

Vishay Product, "BPW34 / BPW34S", Vishay Datasheet 81521, Rev. 2.1; Aug. 23, 2011, 5 pages.

* cited by examiner

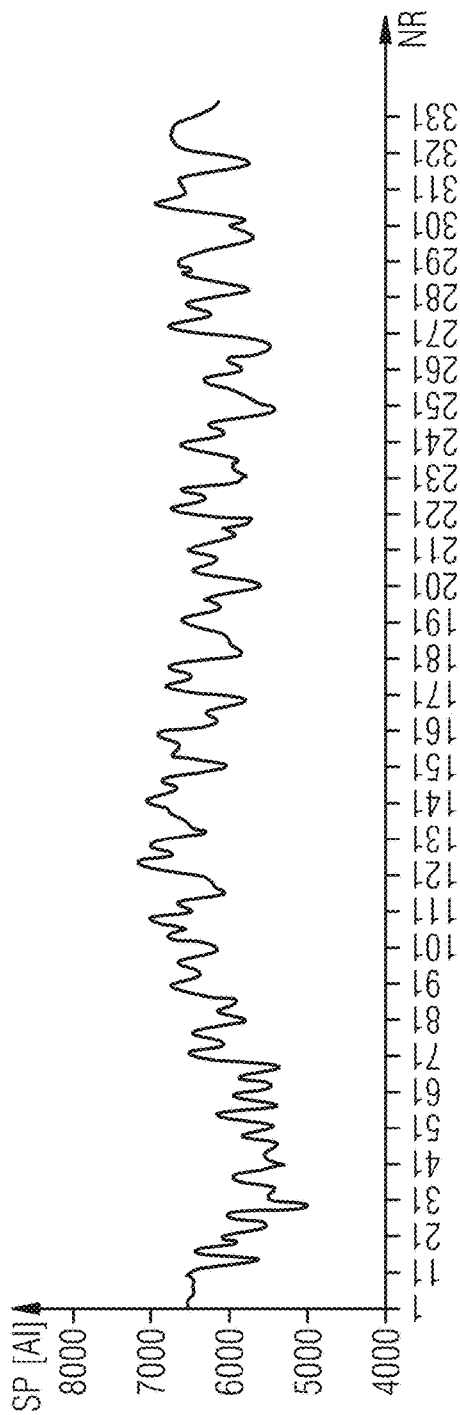
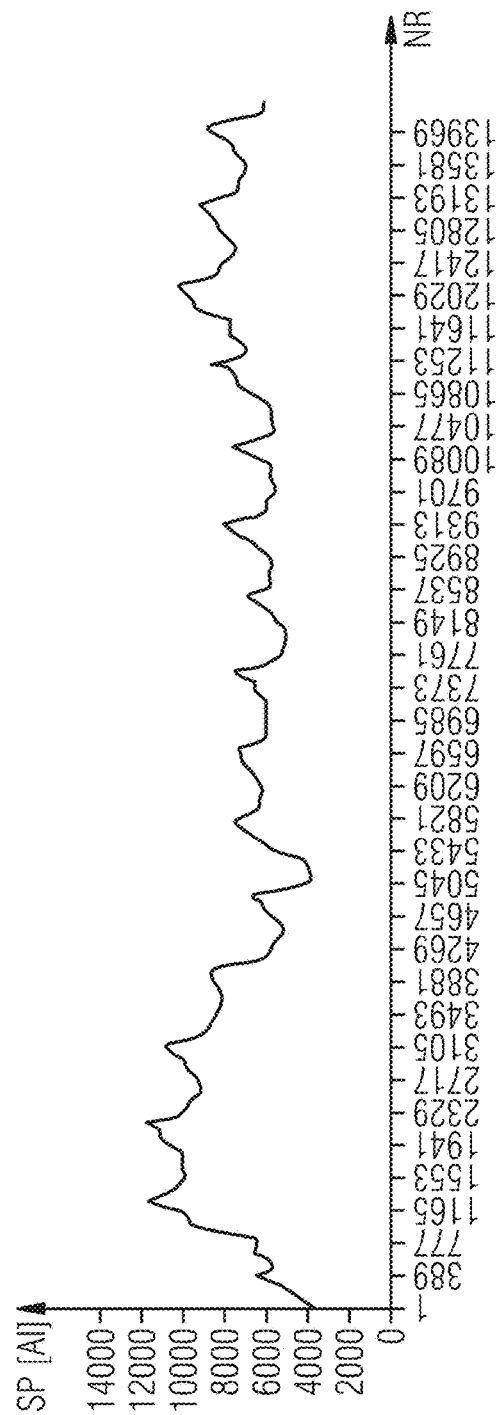

BIOMETRIC SENSOR ARRANGEMENT AND METHOD FOR GENERATING A BIOMETRIC SIGNAL

BACKGROUND OF THE INVENTION

The present application is related to a biometric sensor arrangement and a method for generating a biometric signal.

A biometric sensor arrangement can be configured to determine the heart rate of a user. Such a biometric sensor arrangement comprises one light source and one light sensor to measure pressure changes in the capillaries of the human skin of a user. The light source emits radiation which is spread through the tissue to the capillaries. The light sensor then measures the optical response through the skin. The heart rate can be determined as a function of the optical response. There is an increased demand to realize small and cost-effective biometric sensor arrangements.

SUMMARY OF THE INVENTION

In an embodiment, a biometric sensor arrangement comprises a first and a second radiation source, a driver, a photosensor and a signal conditioning unit. The driver is coupled to the first and the second radiation source and is configured to selectively operate the first and the second radiation source. The signal conditioning unit is coupled to the photosensor and designed to provide a biometric signal.

Advantageously, the first radiation source is combined with the second radiation source and the driver that supplies both the first and the second radiation source. Thus, the driver controls the operating of the first and the second radiation source avoiding an interference between the two radiation sources. At least the first radiation source is used for biometric sensing.

In an embodiment, the second radiation source is implemented as a flash radiation source. The second radiation source may be used for another purpose than biometric sensing. A mobile device typically comprises a radiation source. Thus, the second radiation source may be used for a function of the mobile device. Advantageously, the functions of the biometric sensor arrangement and of the mobile device could be combined.

In an embodiment, the first radiation source is implemented as a black-body radiator, a laser, a lamp such as incandescent lamp or a Nernst lamp, a heater or a light-emitting diode, abbreviated LED.

A radiation emitted by the first radiation source may be a visible light, an ultraviolet light or an infrared light.

In an embodiment, the second radiation source is implemented as a LED, a laser or a lamp.

In an embodiment, the second radiation source may be realized as flash LED. The flash LED is designed to be able to emit a flash. The flash LED is fabricated for conducting a high current. The current flowing through the flash LED may be higher than 200 mA. Alternatively, the current may be higher than 500 mA or 1000 mA.

In an embodiment, the second radiation source is implemented as white flash LED. An area of the die of the second radiation source may be between 0.5 to 4 mm$^2$ or between 1 to 2 mm$^2$.

In an embodiment, the photosensor is configured to provide a photon signal. The photon signal may be a function of radiation emitted by the first radiation source.

In an embodiment, the photosensor is implemented as a photodiode or a phototransistor.

In an embodiment, the signal conditioning unit is configured such that the biometric signal is a function of the photon signal.

In an embodiment, the driver is configured to operate the first radiation source in a first operating phase and to operate the second radiation source in a second operating phase. The first and the second operating phases are free of an overlap. The signal conditioning unit may be configured to provide the biometric signal depending on the photon signal during the first operating phase.

In an embodiment, the signal conditioning unit is configured to provide the biometric signal independent from the photon signal in the second operating phase.

In an embodiment, the second radiation source emits a flash during the second operating phase. The driver is realized to provide a sufficient electric power supply to the second radiation source in the second operating phase.

In an embodiment, the first radiation source is configured to protect the second radiation source, for example in case of an electrostatic discharge event, abbreviated ESD event.

In an embodiment, the first and the second radiation source are both implemented as LED. The first and the second radiation source form an anti-parallel circuit of diodes. Thus, an anode of the first radiation source is connected to a cathode of the second radiation source and a cathode of the first radiation source is connected to an anode of the second radiation source. Since the anti-parallel circuit of the first and the second radiation source only has two terminals, the driver also requires only exactly two driver terminals to supply electric power to the first radiation source as well as to the second radiation source.

In an embodiment, the first radiation source is configured to emit radiation at a first wavelength and the second radiation source is configured to emit radiation at a second wavelength. The first wavelength is different from the second wavelength.

In an embodiment, the signal conditioning unit is configured to provide the biometric signal depending from the photon signal in the first and the second operating phase. The photon signal in the second operating phase may be used for on-line calibration or reducing the influence of disturbing parameters, a baseline or a drift.

In an embodiment, the driver is realized as an H-bridge. The H-bridge is configured to selectively supply the first and the second radiation source.

In an embodiment, the H-bridge comprises a converter, a switch, a current source and a further current source. The H-bridge is configured such that the converter and the current source supply the second radiation source and that the further current source and the switch supply the first radiation source. The current source is arranged between a first driver terminal and a reference potential terminal. The further current source is located between the first driver terminal and a supply terminal. The converter is arranged between the supply terminal and a second driver terminal. The switch is located between the second driver terminal and the reference potential terminal. The first and the second radiation source are coupled between the first and the first driver terminal.

In an alternative embodiment, the driver comprises the current source, the further current source and the converter. The further current source couples the supply terminal to the first driver terminal. The current source couples an output of the converter to the first driver terminal. The first driver terminal is connected to a terminal of the first radiation source and to a terminal of the second radiation source. A further terminal of the first radiation source and a further terminal of the second radiation source may be coupled to the reference potential terminal, for example directly or via the switch. The converter generates a converter voltage. The converter voltage may have an opposite polarity in comparison to a supply voltage tapped at the supply terminal. The converter voltage may be negative with respect to the reference potential terminal. Thus, in the first operating phase, a positive voltage may be applied to the first driver terminal and, in the second operating phase, a negative voltage may be applied to the first driver terminal. Advantageously, the converter is realized as a negative voltage circuit for a p-channel metal-oxide-semiconductor flash current source, abbreviated PMOS Flash current source.

In an embodiment, the driver comprises a signal terminal coupled to a signal terminal of the signal conditioning unit for synchronizing the operation of the first radiation source with the operation of the signal conditioning unit. The signal terminal of the driver may be a signal output terminal and the signal terminal of the signal conditioning unit may be a signal input terminal that is connected to the signal output terminal of the driver.

In an embodiment, the signal conditioning unit comprises a transimpedance amplifier for amplifying the photon signal.

In an embodiment, the first and the second radiation source are located in vicinity of each other. The first and the second radiation source may emit radiation through the same opening or the same transparent window of a housing enclosing the biometric sensor arrangement. Only one opening or transparent window is necessary for the first and the second radiation source. The first and the second radiation source may both be arranged on a common carrier or common substrate.

In a further development, the photosensor receives radiation through the same opening or the same transparent window that is designed for emitting radiation by the first and the second radiation source. Thus, the photosensor may be arranged on the common carrier or the common substrate in vicinity to the first and the second radiation source.

In an embodiment, the biometric sensor arrangement is configured to determine the heart rate of a user, also called pulse of the user. The biometric sensor arrangement is implemented as heart rate sensor, heart rate monitor or photoplethysmograph. The biometric sensor arrangement is designed to measure the normal resting adult human heart rate ranging from 60 to 100 beats per minute, abbreviated bpm, and the heart rate during a tachycardia, also called tachyarrhythmia that is a heart rate exceeding the normal resting rate caused by exercise of a person or by a problem within the heart. The biometric sensor arrangement may be designed to measure heart rates in an interval of 30 bpm to 250 bpm.

Alternatively or additionally, the biometric sensor arrangement is configured to determine at least one parameter in the skin of a user of a group consisting of a melanin concentration, a water concentration, a fat concentration, an alcohol concentration and an oxygen concentration. The oxygen concentration may be a blood oxygen concentration or the oxygen saturation level of arterial blood.

In an embodiment, the biometric sensor arrangement is configured as pulse oximeter that measures the oxygen saturation level as well as the pulse. Thus, the heart rate measurement may be combined with the oxygen measurement.

In an embodiment, a mobile device comprises the biometric sensor arrangement. The mobile device may be realized as a watch or a mobile telecommunication device, such as mobile phone or mobile smartphone. The mobile device may comprise a camera. The camera may be coupled to the second radiation source. Thus, the second radiation source realized as a flash radiation source may be used for the implementation of the camera. The second radiation source may generate a flash for the operation of the camera.

The second radiation source may be implemented into a flash LED radiation source for mobile camera applications. A duration of the flash may be between 5 to 500 ms or between 50 to 200 ms, for example 100 ms.

In an embodiment, a torch may be coupled to the second radiation source. The second radiation source may be implemented for the realization of the torch, for example of the torch of a mobile device.

In an embodiment, a method for generating a biometric signal comprises selectively operating a first and a second radiation source by a driver. The second radiation source may be implemented as a flash radiation source. A photon signal is provided by a photosensor as a function of radiation emitted by the first radiation source. The biometric signal is provided by a signal conditioning unit as a function of the photon signal.

Advantageously, the driver can select the operating of the first and the second radiation source for avoiding an interference of the function which is performed by the first radiation source and the function which is performed by the second radiation source. Light may be a form of radiation.

In an embodiment, the biometric sensor arrangement uses a driver of a flash LED. A signal processing unit of the heart rate sensor is connected either to an integrated sensing photodiode or an external sensing photodiode.

In an embodiment, the driver of a flash LED is implemented as an emission source for biometric sensing.

In an embodiment, the first radiation source is implemented as an ESD Diode of the flash LED in reversed polarity to emit a light of a particular wavelength—such as red, green, IR—and shining it into a living organism to measure biometric signals, for example heart rate.

In an embodiment, the driver is designed either as an H-Bridge circuit with current sink/source. Alternatively, the driver comprises a negative voltage circuit for a p-channel metal-oxide-semiconductor flash current source, abbreviated PMOS Flash current source. The H-Bridge may be realized as analog H-Bridge.

In an embodiment, the driver synchronizes the emission of a biometric sensing process with an external photo measurement device, such as a photodiode.

In an embodiment, the first radiation source is implemented as a reversed ESD diode which does emit an optical signal for measuring biometric information of a living object.

In an embodiment, the second radiation source indicates to a user where to put his finger when he wants to measure his heart rate. A switching occurs between a flash indication pulse provided by the second radiation source and a pulse provided by the first radiation source for measurement of heart rate.

In an embodiment, the biometric sensor arrangement is configured for the measurement of a biometric signal such as for example melanin, water, fat, alcohol, heartrate and blood oxygen.

The first radiation source may emit light with a wavelength between 300 nm to 700 nm for the detection of melanin. A group of natural pigments found in most organism is called melanin.

The first radiation source may emit light with a wavelength between 1150 nm to 2000 nm—such as 1600 nm— for the measurement of water. A small water concentration may be a hint of a dehydration of a user.

The first radiation source may emit light with a wavelength between 1000 nm to 2000 nm for the detection of fat.

In an embodiment, the biometric sensor arrangement is realized as pulse oximeter. The first radiation source may emit light with a wavelength between 500 nm to 1000 nm for the detection of blood oxygen. The first radiation source may emit infrared light, for example with a wavelength of 890 nm or 950 nm. The second radiation source or a third radiation source comprised by the biometric sensor arrangement may emit red light, for example at 650 nm or 663 nm. The oxygen saturation level of blood may be calculated as a function of the photon signal received in response to the infrared light and of the photon signal received in response to the red light.

In an embodiment, a synchronization signal is generated for the synchronization of the driver and the photodiode that senses the biometric signal and is integrated with a signal conditioning unit.

BRIEF DESCRIPTION OF THE DRAWINGS

The following description of figures may further illustrate and explain exemplary embodiments. Insofar as components, circuits and method steps correspond to one another in terms of their function in different figures, the description thereof is not repeated for each of the following figures.

FIGS. 1A to 1G show an exemplary embodiment of a biometric sensor arrangement;

DETAILED DESCRIPTION

Figure 1A:
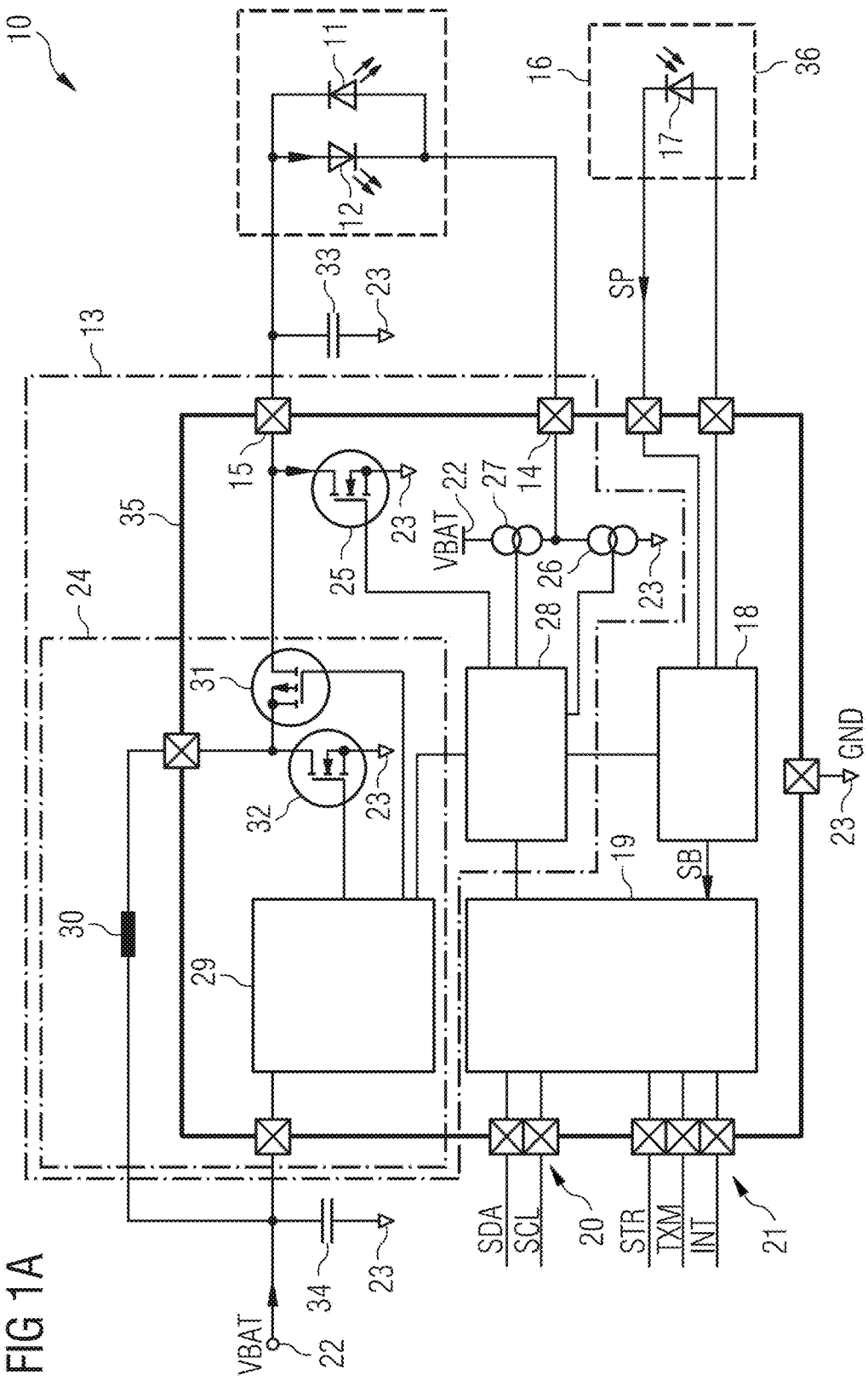

FIG. 1A shows an exemplary embodiment of a biometric sensor arrangement 10 which comprises a first radiation source 11 and a second radiation source 12. Moreover, the biometric sensor arrangement 10 comprises a driver 13 that is connected to the first and the second radiation source 11, 12. A first driver terminal 14 of the driver 13 is connected to first terminals of the first and the second radiation source 11, 12. A second driver terminal 15 of the driver 13 is connected to second terminals of the first and the second radiation source 11, 12. The first and the second radiation source 11, 12 emit radiation, the radiation may be light.

The second radiation source 12 may be fabricated as a flash radiation source. Thus, the second radiation source 12 may be configured to emit a flash of visible light, for example white light. The second radiation source 12 may be designed to conduct a pulse current higher than 200 mA, alternatively higher than 500 mA or 1 A.

The first and the second radiation source 11, 12 are realized as light-emitting diodes, abbreviated LEDs. The first radiation source 11, for example, is realized as infrared LED. The first radiation source 11 is designed as an electrostatic discharge protection diode, abbreviated ESD diode. The second radiation source 12 may be implemented as white LED.

The first and the second radiation source 11, 12 are configured as an anti-parallel circuit of diodes. An anode of the first radiation source 11 is directly connected to a cathode of the second radiation source 12. An anode of the second radiation source 12 is directly connected to a cathode of the first radiation source 11. Thus, the anode of the first radiation source 11 and the cathode of the second radiation source 12 are connected to the first driver terminal 14. The anode of the second radiation source 12 and the cathode of the first radiation source 11 are connected to the second driver terminal 15.

Additionally, the biometric sensor arrangement 10 comprises a photosensor 16. The photosensor 16 comprises a photodiode 17. The biometric sensor arrangement 10 comprises a signal conditioning unit 18 that is coupled to the photosensor 16 and, thus, to the photodiode 17. The signal conditioning unit 18 is connected to two terminals of the photodiode 17. The photodiode 17 may be implemented as BPW34 diode fabricated by Vishay Intertechnology, Inc. or OSRAM Opto Semiconductors GmbH, Regensburg, Germany.

Furthermore, the biometric sensor arrangement 10 comprises a logic circuit 19. The logic circuit 19 is connected to the signal conditioning unit 18. The logic circuit 19 may be realized as an inter-integrated circuit, abbreviated I2C circuit. The logic circuit 19 may comprise registers. The biometric sensor arrangement 10 comprises an inter-integrated circuit interface 20, abbreviated I2C interface, connected to the logic circuit 19, as well as further signal terminals 21, connected to the logic circuit 19. The biometric sensor arrangement 10 is connected to a supply terminal 22 and to a reference potential terminal 23.

The driver 13 is realized as an H-bridge. The driver 13 comprises a converter 24. The converter 24 is realized as a DC-to-DC converter. The converter 24 is coupled between the supply terminal 22 and the second driver terminal 15. Moreover, the driver 13 comprises a switch 25. The switch 25 couples the second driver terminal 15 to the reference potential terminal 23. The switch 25 may be realized as a field-effect transistor. The switch 25 may be implemented as an n-channel metal-oxide-semiconductor field-effect transistor.

Furthermore, the driver 13 comprises a current source 26 that couples the first driver terminal 14 to the reference potential terminal 23. Additionally, the driver 13 comprises a further current source 27 that is arranged between the supply terminal 22 and the first driver terminal 14. The driver 13 comprises a control unit 28. The control unit 28 may be designed as a state machine. Alternatively, the control unit 28 may be implemented by a microprocessor or a microcontroller. The control unit 28 can be realized as heart rate control unit. The control unit 28 is connected to a control terminal of the switch 25 and a control terminal of the further current source 27. Additionally, the control unit 28 may also be connected to a control terminal of the current source 26. Furthermore, the control unit 28 can also be connected to a control terminal of a converter controller 29 of the converter 24, the signal conditioning unit 18 and the logic circuit 19. A driver capability of the current source 26 may be larger than a driver capability of the further current source 27.

The converter 24 is implemented as an inductive DC-to-DC converter. The converter 24 is realized as a step-up or Boost converter. The converter 24 comprises an inductor 30 having a first terminal connected to the supply terminal 22. A second terminal of the inductor 30 is coupled via a first converter switch 31 of the converter 24 to the second driver terminal 15. The second terminal of the inductor 30 is coupled via a second converter switch 32 of the driver 24 to the reference potential terminal 23. An output capacitor 33 couples the first terminal 15 to the reference potential terminal 23. An input capacitor 34 is arranged between the supply terminal 22 and the reference potential terminal 23. The converter controller 29 is connected to the control terminal of the first and the second converter switch 31, 32 and to the supply terminal 22. The first and the second converter switch 31, 32 are realized as field-effect transistors.

The signal conditioning unit 18, the control unit 28, the logic circuit 19, the current source 26, the further current source 27, the switch 25 and parts of the converter 24 are integrated on a semiconductor substrate 35. The first and the second converter switch 31, 32 and the converter controller 29 are integrated on the semiconductor substrate 35. The photosensor 16 is not implemented on the semiconductor substrate 35. The semiconductor substrate 35 is free of any photosensor. Also the first and the second radiation source 11, 12, the supply capacitor 34 and the output capacitor 33 are not integrated on the semiconductor substrate 35. Furthermore, the inductor 30 of the converter 24 is not realized on the semiconductor substrate 35.

The biometric sensor arrangement 10 comprises a further semiconductor substrate 36. The photosensor 16 is integrated on the further semiconductor substrate 36.

As the further semiconductor substrate 36 with the receiving photodiode 17 is not having any analog amplification circuitry, a cost improvement due to regular diode process is achieved. Realizing the photodiode 17 without integration with another circuit, the size of the photodiode 17 can be bigger as there is no cost pressure which does improve an optical integration of movement fractures. This results in a better signal quality.

Figure 1B:
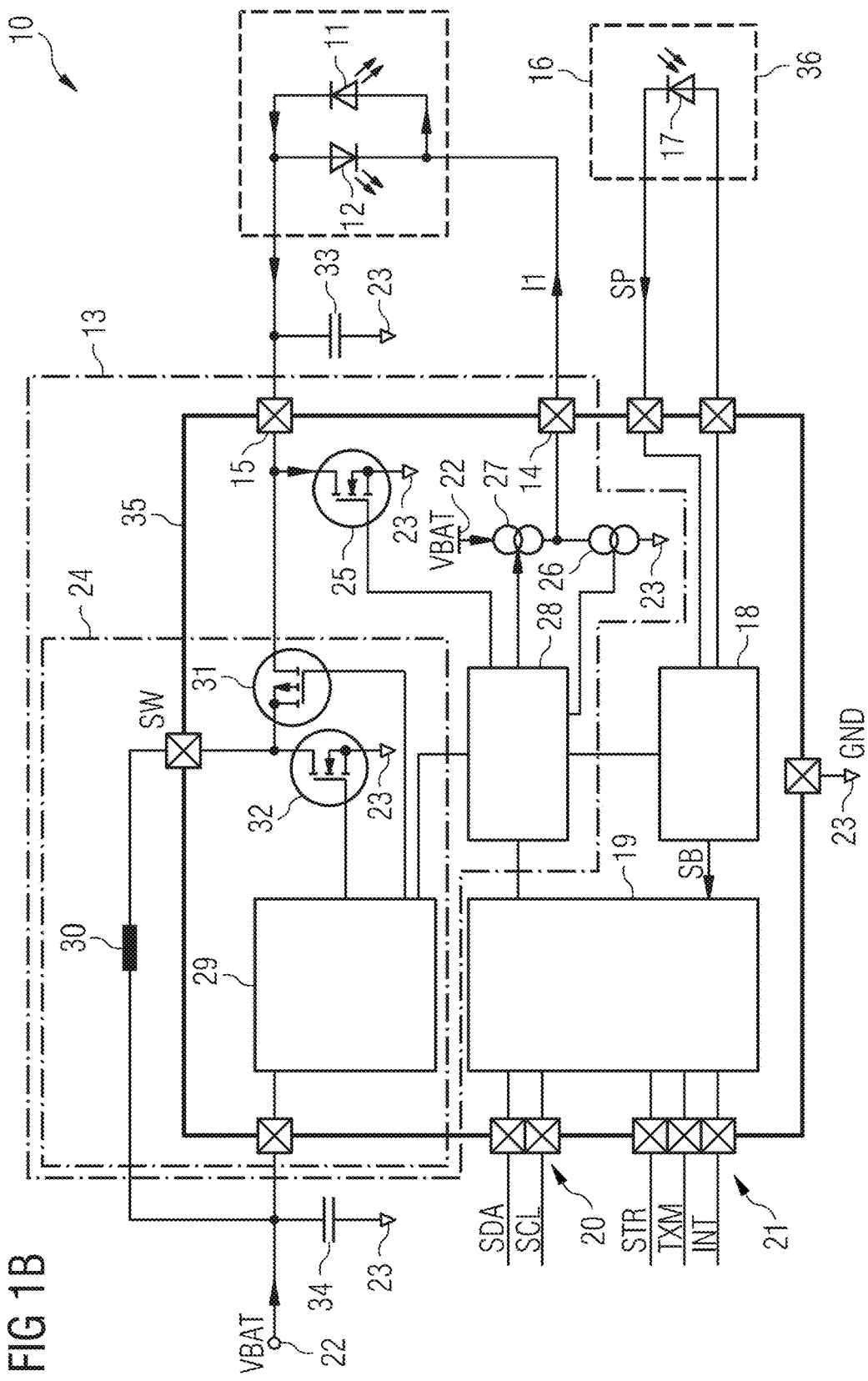
Figure 1C:
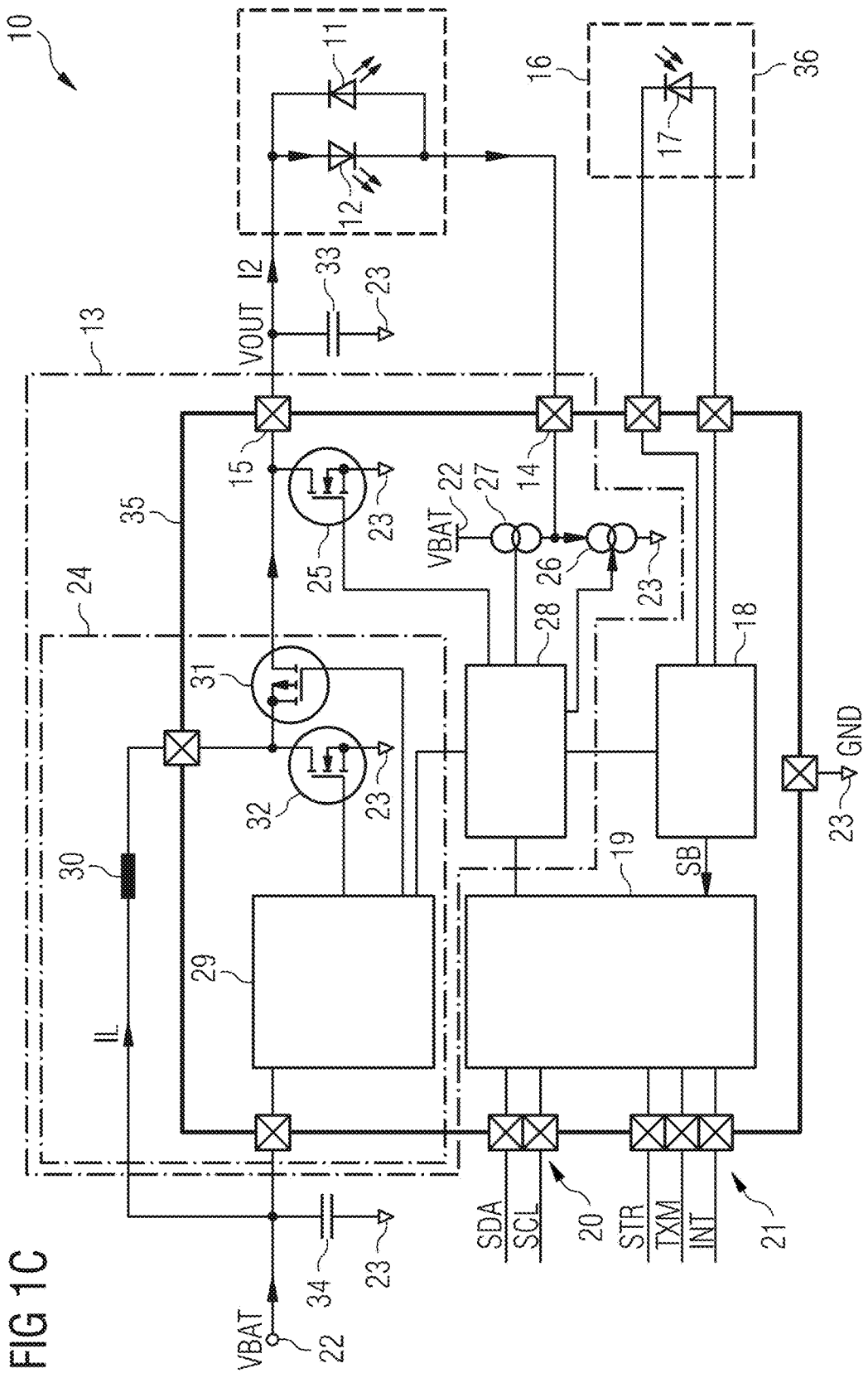

The signals and the operation of the biometric sensor arrangement 10 is explained using FIGS. 1B and 1C. The biometric sensor arrangement 10 is operated in a first operating phase A and in a second operating phase B. The first operating phase A is shown in FIG. 1B, whereas the second operating phase B is shown in FIG. 1C.

In an alternative, not shown embodiment, the converter 24 may be realized as a capacitive DC-to-DC converter.

In an alternative, not shown embodiment, the converter 24 may be realized as step-down or step-up/step-down converter, also named Buck or Buck-Boost converter.

Alternatively, the second radiation source 12 does not operate as a flash radiation source. For example, the second radiation source 12 may contribute to the detection of a parameter of a user by the first radiation source 11 and the photosensor 16 or may operate as backlight of a display or as an indicator light.

FIG. 1B shows the first operating phase A of the biometric sensor arrangement 10 illustrated in FIG. 1A. A battery voltage VBAT is provided to the supply terminal 22. A reference potential GND is tapped at the reference potential terminal 23. A first and a second I2C signal SDA, SCL are applied at the two terminals of the I2C interface 20. The further signals STR, TXM, INT are applied at the further signal terminals 21 and, thus, at the logic unit 19. The control unit 28 controls the first and the second operating phase A, B. In the first operating phase A, the converter 24 and the current source 26 are deactivated by the control unit 28. In the first operating phase A, no current flows through the converter 24 and the current source 26.

In the first operating phase A, the further current source 27 is activated and the switch 25 is set in a conducting state by the control unit 28. The polarity of the first radiation source 11 is designed such that a first current I1 can flow through the first radiation source 11. Thus, the first current I1 is controlled by the further current source 27 and flows through the first radiation source 11 and the switch 25. Therefore, the first current I1 flows from the supply terminal 22 via the further current source 27, the first driver terminal 14, the first radiation source 11, the second driver terminal 15 and the switch 25 to the reference potential terminal 23.

In the first operating phase A, no current flows through the second radiation source 12. The polarity of the second radiation source 12 is designed such that the first current I1 cannot flow through the second radiation source 12 in the first operating phase A.

During the first operating phase A, the photodiode 17 of the photosensor 16 generates a photon signal SP that is provided to the signal conditioning unit 18. The signal conditioning unit 18 generates a biometric signal SB that is provided to the logic circuit 19. The logic circuit 19 delivers the information comprised by the biometric signal SB via the I2C terminals 20 or the further signal terminals 21 to a not shown microprocessor, microcontroller or computer.

Alternatively, the signal conditioning unit 18 performs an analog signal conversion or analog and digital signal conversion of the photon signal SP. The signal conditioning unit 18 provides a modified photon signal SP' to the logic circuit 19. The logic circuit 19 generates the biometric signal SB. The logic circuit 19 delivers the biometric signal SB via the I2C terminals 20 or the further signal terminals 21 to a not shown microprocessor, microcontroller or computer.

FIG. 1C shows the second operating phase B of the biometric sensor arrangement 10 illustrated in FIGS. 1A and 1B. In the second operating phase B, the switch 25 is set in a non-conducting state by the control unit 28. Additionally, the further current source 27 is deactivated by the control unit 28. The control unit 28 activates the converter 24. For this purpose, the control unit 28 provides a signal to the converter controller 29. In the second operating phase B, the converter 24 performs a DC/DC conversion of the battery voltage VBAT into an output voltage VOUT. The output VOUT can be tapped between the second driver terminal 15 and the reference potential terminal 23. The output voltage VOUT is applied across the output capacitor 33.

The second converter switch 32 is set in a conducting state and the first converter switch 31 is set in a non-conducting state in a first converter phase B1 of the converter 24. The battery voltage VBAT mainly drops across the inductor 30. Thus, an inductor current IL that flows through the inductor 30 rises in the first converter phase B1. The inductor current IL flows from the supply terminal 22 via the inductor 30 and the second converter switch 32 to the reference potential terminal 23 in the first converter phase B1.

In a second converter phase B2, the first converter switch 31 is set in a conducting state and the second converter switch 32 is set in a non-conducting state. The second converter phase B2 follows the first converter phase B1. In the second converter phase B2, the inductor current IL flows from the supply terminal 22 through the inductor 30 and the first converter switch 31 to the output of the converter 22 and charges the output capacitor 33. Thus, the output voltage VOUT is increased during the second converter phase B2.

The converter controller 29 controls the first and the second converter switch 31, 32. The first and the second converter phases B1, B2 are periodically repeated, for example with a frequency of 4 MHz. The output voltage VOUT will be increased until the output voltage VOUT obtains a value sufficient for a flash provided by the second radiation source 12.

In the second operating phase B, the second radiation source 12 provides a flash, when the current source 26 is triggered by the control unit 28. Thus, the flash occurs in a flash operating period B3 after repeating the first and the second converter phase B1, B2 several times. During the flash operating period B3, a second current I2 flows through the second radiation source 12 generating the flash of light. The second current I2 is controlled by the current source 26. During the flash operating period B3, the second current I2 flows from the output capacitor 33 via the second radiation source 12, the first driver terminal 14 and the current source 26 to the reference potential terminal 23.

By the flash of the second radiation source 12, the output voltage VOUT is decreased. However, the value of the output voltage VOUT may still be higher than 0 V. At the start of the next first operating phase A, the output voltage VOUT is set to zero by the switch 25.

Figure 1D:
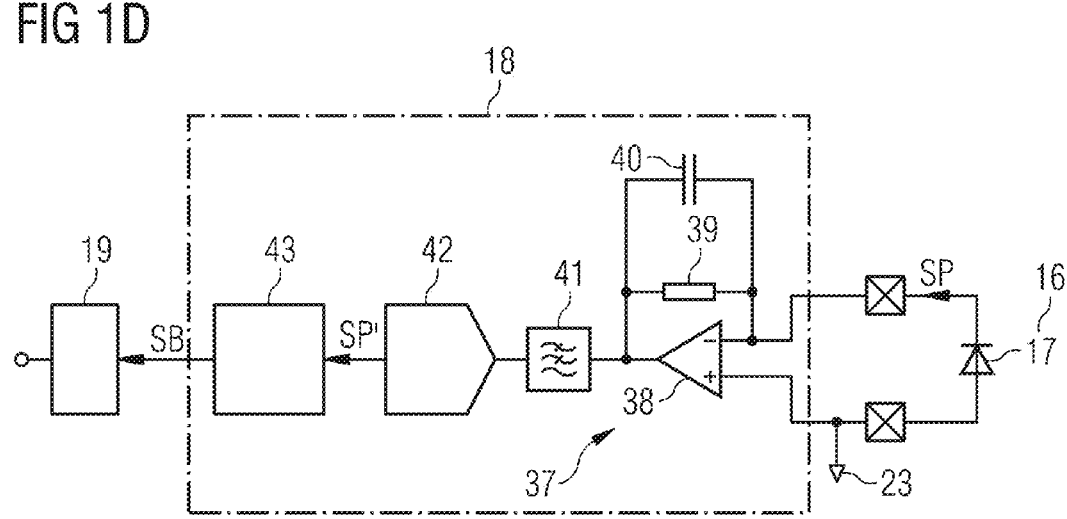

FIG. 1D shows an exemplary embodiment of the signal conditioning unit 18 of the biometric sensor arrangement 10 shown in FIG. 1A to 1C. The signal conditioning unit 18 comprises a transimpedance amplifier 37 that is connected on its input side to the photosensor 16. The photodiode 17 is connected to the input of the transimpedance amplifier 37.

The transimpedance amplifier 37 comprises an operational amplifier 38. A feedback resistor 39 couples a first input of the operational amplifier 38 to an output of the operational amplifier 38. Moreover, a feedback capacitor 40 is arranged between the first input of the operational amplifier 38 and the output of the operational amplifier 38. A terminal of the photodiode 17 is connected to the first input of the operational amplifier 38. A further terminal of the photodiode 17 and a second input of the operational amplifier 38 are connected to the reference potential terminal 23. The output of the operational amplifier 38 is connected to an output of the transimpedance amplifier 37. The first input of the operational amplifier 38 is realized as an inverting input and the second input of the operational amplifier 38 is implemented as a non-inverting input.

Furthermore, the signal conditioning unit 18 comprises an analog-to-digital converter 42 coupled to the output of the transimpedance amplifier 37. The signal conditioning unit 18 comprises a filter 41 coupling the output of the transimpedance amplifier 37 to the analog-to-digital converter 42. The filter 41 may be realized as a low-pass filter. Moreover, the signal conditioning unit 18 may comprise a calculation unit 43. The calculation unit 43 is connected on its input side to the analog-to-digital converter 42. The calculation unit 43 is coupled on its output side to the logic circuit 19.

The photon signal SP is provided to the transimpedance amplifier 37. The analog-to-digital converter 42 generates a modified photon signal SP∝. The calculation unit 43 generates the biometric signal SB as a function of the photon signal SP. The calculation unit 43 may comprise a state machine, a microcontroller or a microprocessor.

As the transimpedance amplifier 37 can be driven by a bigger photodiode 17, a lower gain of the transimpedance amplifier 37 can set. This results in a better signal-to-noise ratio inside the signal conditioning circuit 18.

In an alternative, not shown embodiment, the signal conditioning unit 18 does not comprise a calculation unit 43. The analog-to-digital converter 42 is connected to the logic circuit 19. The logic circuit 19 calculates the biometric signal SB.

Figure 1E:
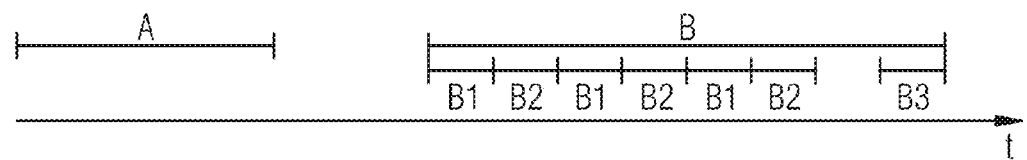

FIG. 1E show an exemplary embodiment of the operating phases of the biometric sensor arrangement 10. In an example, the biometric sensor arrangement 10 first operates in the first operating phase A and then in the second operating phase B. When the second operating phase B starts, then the converter 24 generates the output voltage VOUT by a sequence of the first and the second converter phases B1, B2. After this sequence of the first and the second converter phases B1, B2, a flash is emitted by the second radiation source 12 during the flash operating phase B3. The first operating phase A and the second operating phase B do not overlap. There may be an idle phase between the first and the second operating phase A, B.

Other sequences are possible: The biometric sensor arrangement 10 may operate using more than one first operating phase A until it operates using the second operating phase B. Alternatively, the biometric sensor arrangement 10 may operate using one or more than one second operating phase B until it operates using the first operating phase A. The sequence of the first and the second converter phases B1, B2 may consist of exactly one first converter phase B1 and of exactly one second converter phase B2.

FIGS. 1F and 1G show examples of measurements of different embodiments of the biometric sensor arrangement 10. In FIGS. 1F and 1G, the response of the photodiode 17 in artificial units A1 is illustrated as a function of a measurement number NR. The photodiode 17, used to obtain the measurement results shown in FIG. 1F, has an area of 7.5 mm$^2$, whereas the area of the photodiode 17 used for the measurement shown in FIG. 1G has a value of 1 mm$^2$. A photodiode 17 with a 7.5 mm$^2$ area improves the optical performance compared to a photodiode 17 with 1 mm$^2$ area, because more light is received shining through capillaries; therefore, the signal to noise ratio is improved. The ratio con also be named signal to baseline ratio, since the signal generated by a pulse of a user has to be detected in the presence of a signal generated for example by optical refraction from the surface of the skin forming the baseline. A bigger diode area helps to receive a cleaner photon signal SP in the presence of slight body movements because the refractions are "averaged" more.

Figure 2A:
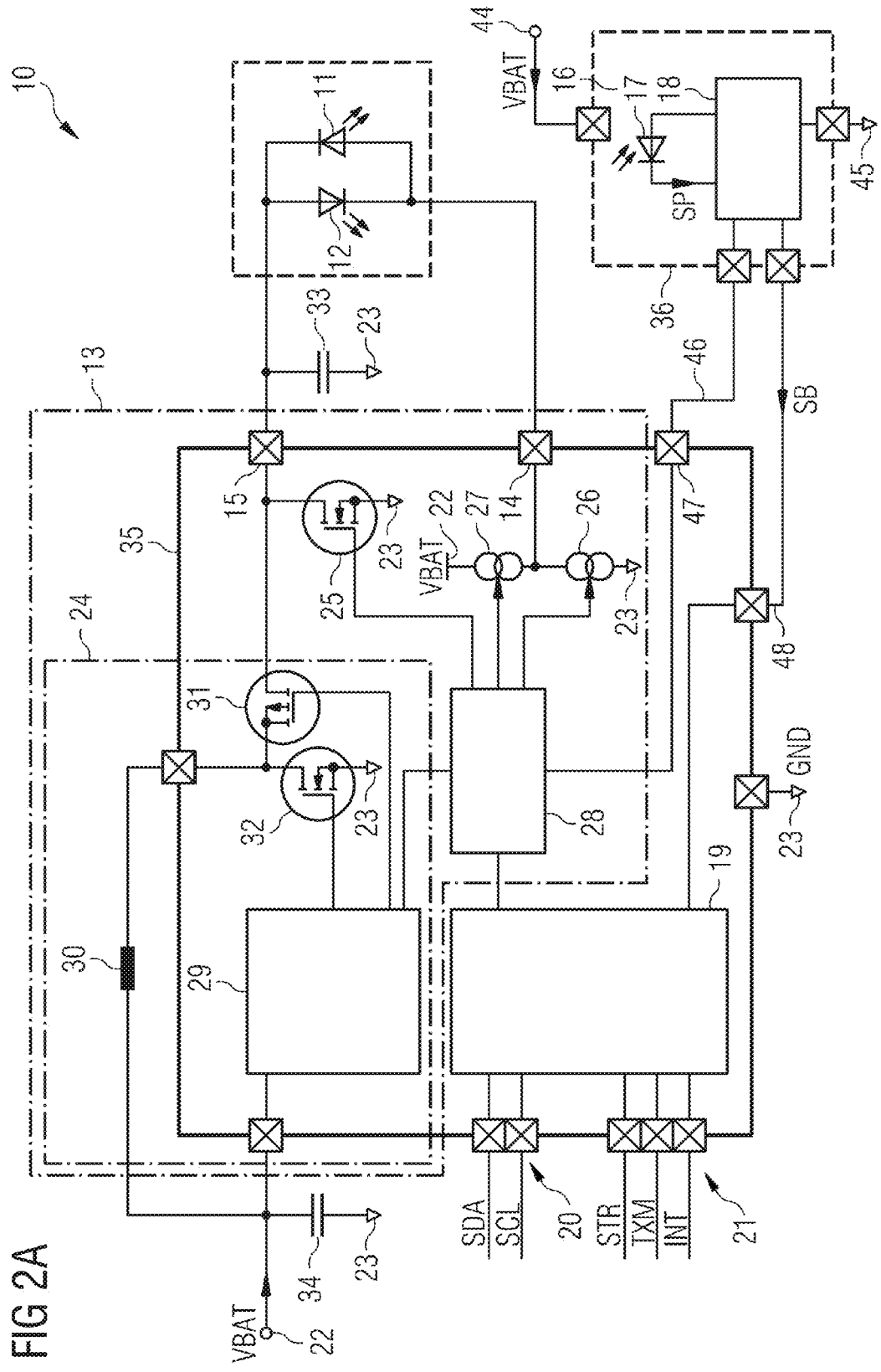
FIGS. 2A to 2D show alternative exemplary embodiments of a biometric sensor arrangement.

FIG. 2A shows an alternative exemplary embodiment of the biometric sensor arrangement 10 which is a further development of the embodiments shown in FIGS. 1A to 1G. The signal conditioning unit 18 and the photosensor 16 are integrated on the further semiconductor substrate 36. The photosensor 16 is realized as the photodiode 17. The further semiconductor substrate 36 has a further supply terminal 44 that is coupled to the supply terminal 22 and a further reference potential terminal 45 connected to the reference potential terminal 23. The control unit 28 is coupled to the signal conditioning unit 18 via a synchronization connection line 46 und a synchronization pin 47. A data connection line 48 may connect the signal conditioning unit 18 to the logic circuit 19 for providing the biometric signal SB to the logic circuit 19.

The further semiconductor substrate 36 realizes the photodiode 17 with an integrated signal conditioning unit 18. Advantageously, a disturbance of the photon signal SP is kept low since the connection lines between the signal conditioning unit 18 and the photodiode 17 can be kept very short. The biometric sensor arrangement 10 is realized with the flash LED driver 13 coupled via the synchronization pin 47 to the photodiode 17 with integrated signal conditioning.

Figure 2B:
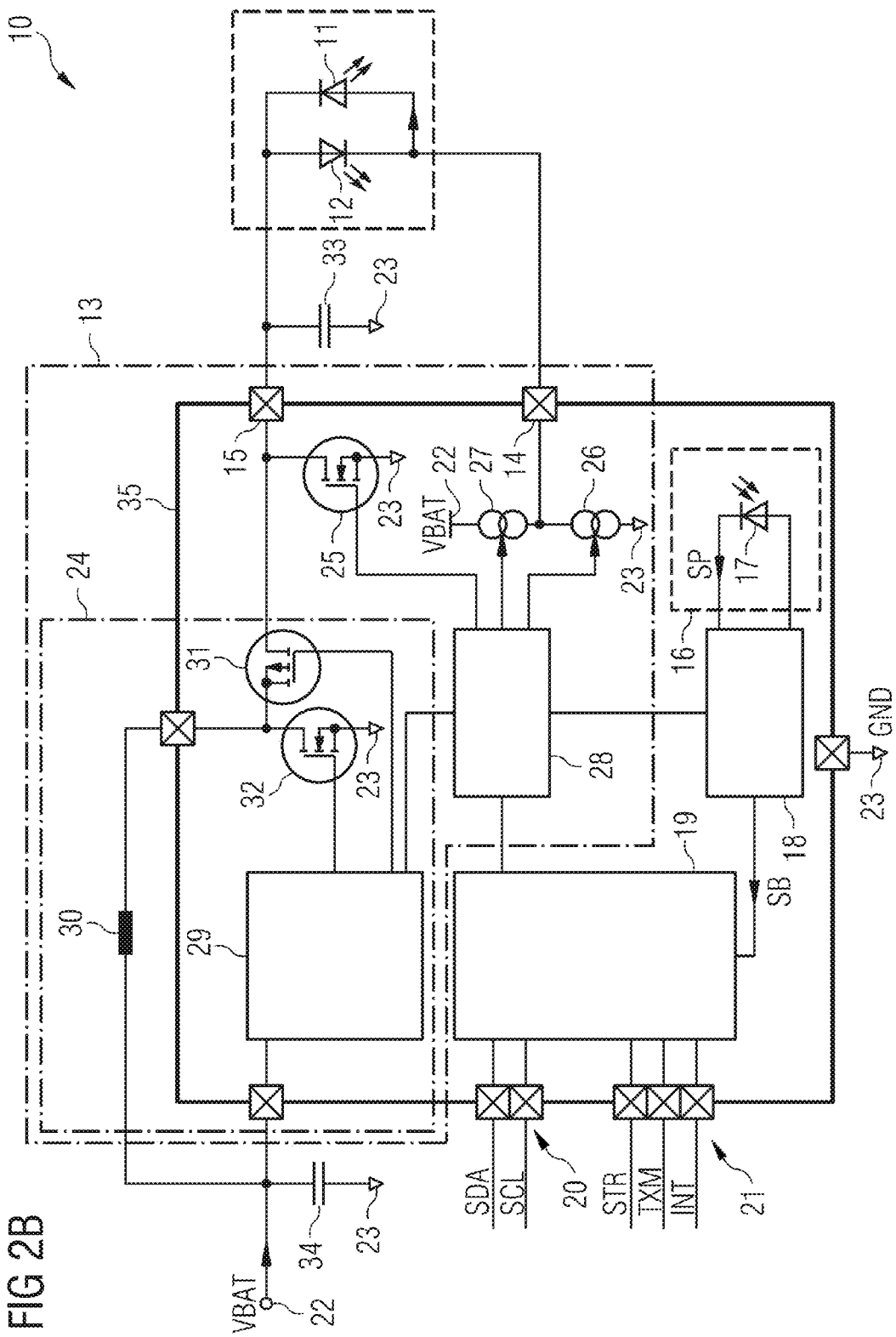

FIG. 2B shows a further exemplary embodiment of the biometric sensor arrangement 10 which is a further development of the embodiments shown in FIGS. 1A to 1G and 2A. The semiconductor substrate 35 also comprises the photosensor 16 having the photodiode 17. Thus, the photosensor 16 is integrated on the semiconductor substrate 35. The semiconductor substrate 35 comprises an integrated photodiode 17. Therefore, the number of pins or pads for the connection of the semiconductor substrate 35 to other components is reduced. Advantageously, the reduced numbers of pins and the reduced length of connection lines result in an increase of the accuracy of the measurements provided by the photodiode 17. The semiconductor substrate 35 comprises the photodiode 17 with the signal conditioning unit 18. The biometric sensor arrangement 10 is implemented as a heart rate sensor with integrated photodiode 17 to use the flash LED as the emitting source 12.

Figure 2C:
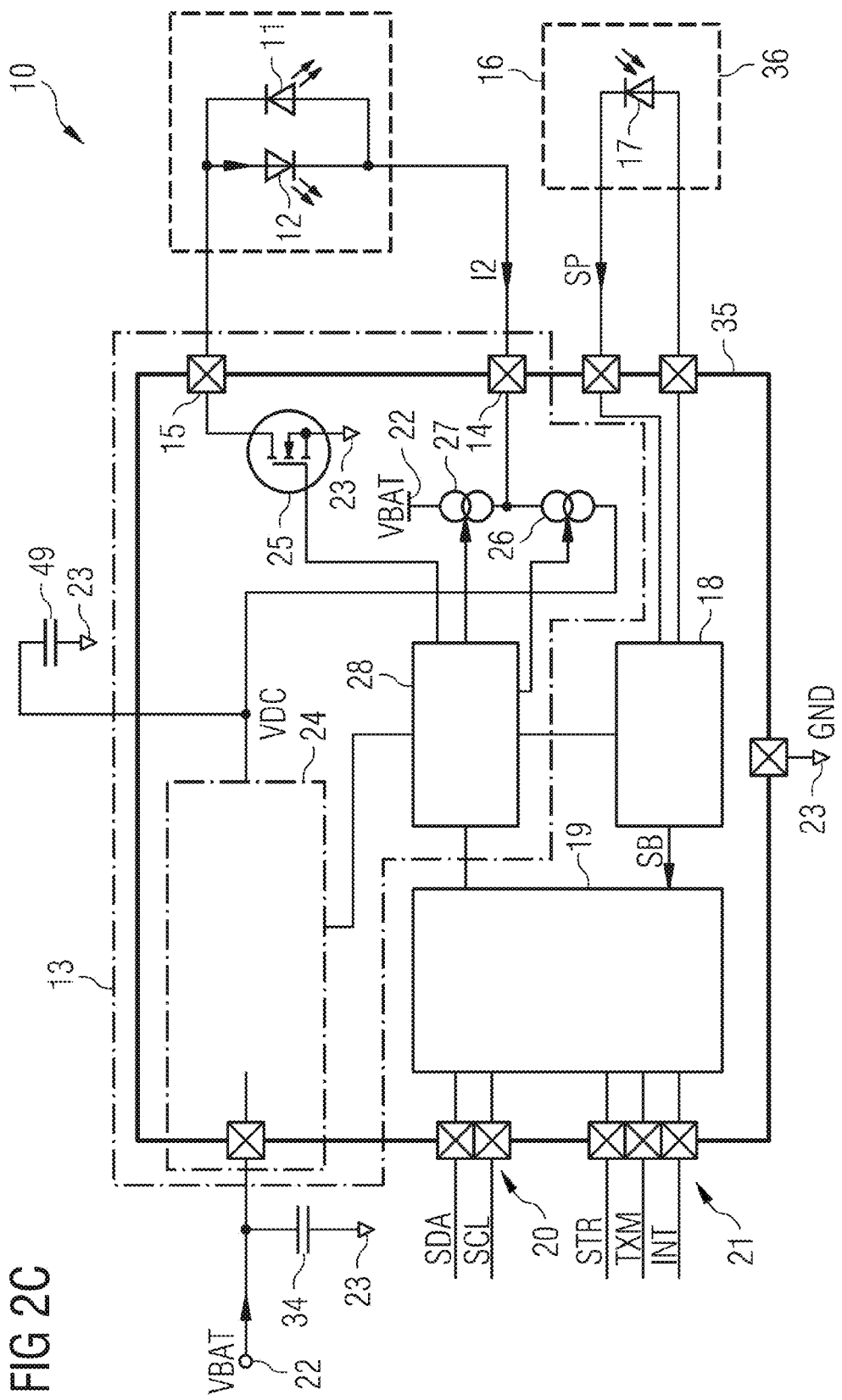

FIG. 2C shows a further exemplary embodiment of the biometric sensor arrangement 10 which is a further development of the embodiments shown in FIGS. 1A to 1G, 2A and 2B. The converter 28 generates a converter voltage VDC. The converter voltage VDC is negative with respect to the reference potential GND. The converter 24 is connected to the cathode of the second radiation source 12. Thus, for example, the output of the converter 24 is connected via the current source 26 to the second radiation source 12. A converter capacitor 46 is connected between the output of the converter 24 and the reference potential terminal 23.

In the second operating phase B, the converter 24 generates the converter voltage VDC. The converter capacitor 46 stabilizes the converter voltage VDC. When the value of the converter voltage VDC is sufficient for generating a flash, the control unit 28 sets the switch 25 in a conducting state and activates the current source 26 for triggering the flash. During the flash the second current I2 flows from the converter capacitor 49 through the current source 26, the first driver terminal 14, the second radiation source 12, the second driver terminal 15 and the switch 25 to the reference potential terminal 23. The output capacitor 33 may be omitted. The operation of the biometric sensor arrangement 10 in the first operating phase A is shown in FIG. 1B.

Figure 2D:
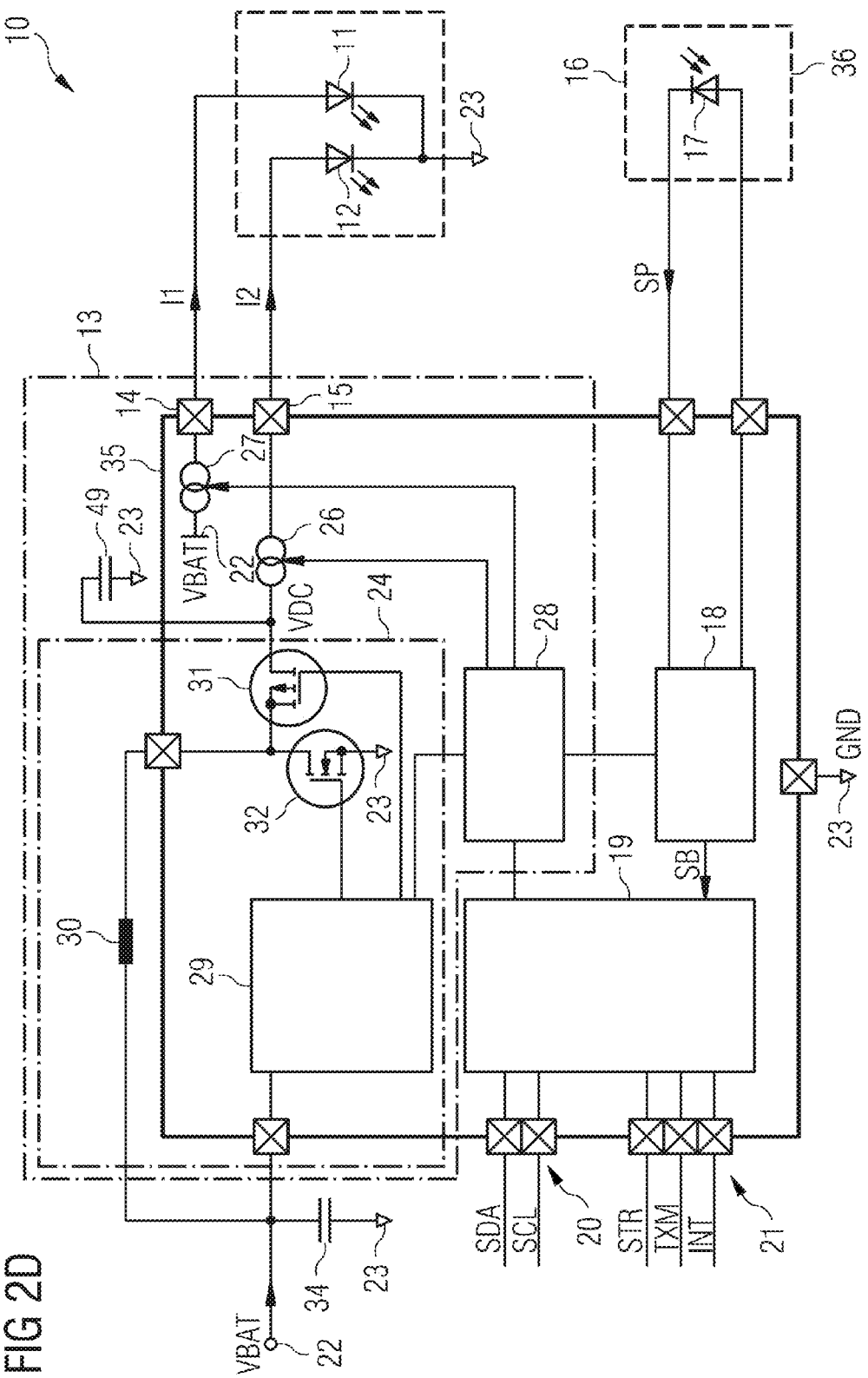

FIG. 2D shows a further exemplary embodiment of the biometric sensor arrangement 10 which is a further development of the embodiments shown in FIGS. 1A to 1G and 2A to 2C. The first and the second radiation source 11, 12 are not arranged as an anti-parallel circuit of diodes. The supply terminal 22 is coupled via the further current source 27, the first driver terminal 14 and the first radiation source 11 to the reference potential terminal 23. The converter 24 is coupled via the current source 26, the second driver terminal 15 and the second radiation source 12 to the reference potential terminal 23. Thus, the anode of the first radiation source 11 is not connected to the anode of the second radiation source 12. The cathode of the first radiation source 11 is connected to the cathode of the second radiation source 12 and to the reference potential terminal 23.

In the first operating phase A, the further current source 27 is actuated and the current source 26 is deactivated. Thus, the first current I1 flows through the first radiation source 11 and the further current source 27.

In the second operating phase B, the further current source 27 is deactivated. First the converter 24 charges the converter capacitor 49. When the output voltage VOUT obtains a value sufficient for a flash, the current source 26 is activated. Thus, the second current I2 flows from the converter capacitor 49 via the current source 26 and the second radiation source 12 to the reference potential terminal 23. Since the control unit 28 controls the first and the second operating phase A, B, a simultaneous emitting of light by both radiation sources 11, 12 is avoided.

Figure 3A:
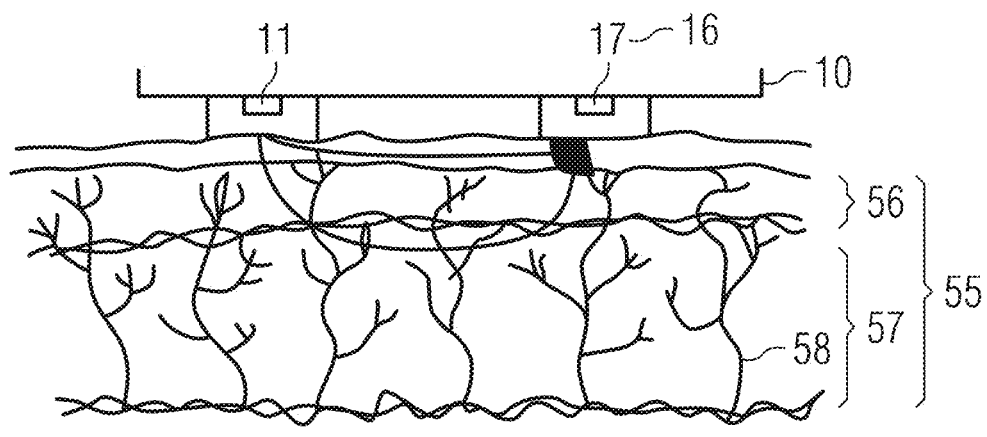
FIGS. 3A to 3E show an exemplary embodiment of an interaction of a biometric sensor arrangement with a user and of mobile devices comprising a biometric sensor arrangement.
Figure 3A:
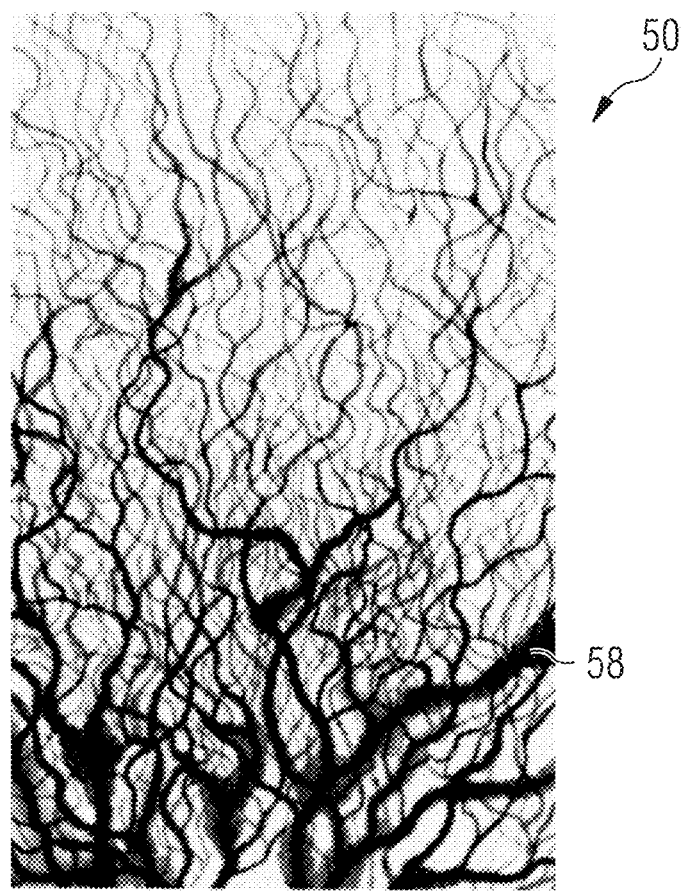

FIG. 3A shows an exemplary embodiment of an interaction of the biometric sensor arrangement 10 with a user. Thus, the procedure of the heartrate measurement is illustrated. In the upper drawing, the first radiation source 11 emits light to a skin 55 of a user. The skin 55 comprises several layers such as an epidermis layer 56 and a hypodermis layer 57. The light emitted by the first radiation source 11 at least penetrates the epidermis layer 56. Capillaries 58 in the skin 55 will change its volume due to the pressure change caused by a pulse of the user. Thus, the light that is detected by the photosensor 16 depends on the volume of the capillaries 58 and, thus, on the pulse of the user. In the lower drawing, an examples of the different capillaries 58 are shown.

The concept is to have one light emitter realized as the first radiation source 11 and one receiver realized as the photosensor 16 having the photodiode 17 to measure the pressure changes in the capillaries 58. The first radiation source 11 emits light such as green, red or IR-light which is spread though the tissue to the capillaries 58. The photosensor 16—also named photo transducer—measures the optical response through the human skin 55. The photosensor 16 can be implemented for example with analogue photodiodes with external transimpedance converters as shown in FIG. 2A or with integrated photodiodes as shown in FIG. 2B. The first radiation source 11 may emit radiation with a wavelength between 480 nm to 950 nm.

Figure 3B:
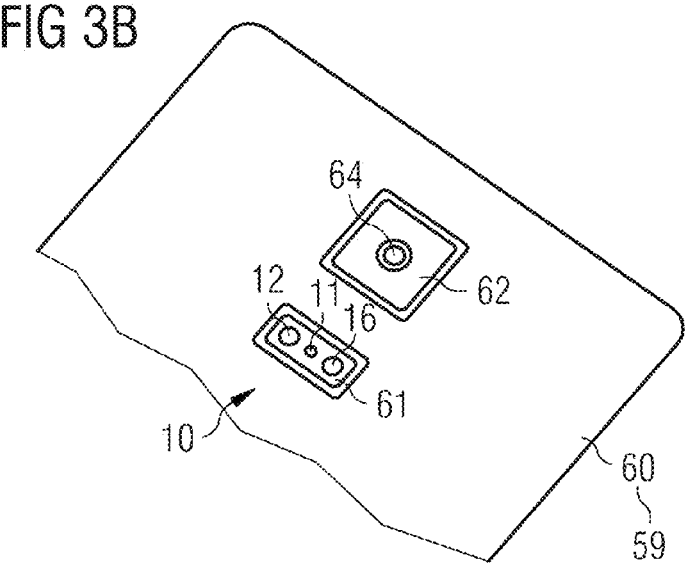

FIG. 3B shows an exemplary embodiment of a mobile device comprising the biometric sensor arrangement 10 that can be realized as illustrated in one of the FIGS. 1A to 1G, 2A to 2D and 3A. The mobile device is realized as mobile telecommunication device 59. The mobile telecommunication device 59 comprises the biometric sensor arrangement 10. The mobile telecommunication device 59 comprises a housing 60 or cover. The housing 60 has an opening 61 that is covered by a transparent window. At the inside of the housing 60, the first and the second radiation source 11, 12 and the photosensor 16 are located. The housing 60 comprises a further opening 62 that is also closed by a transparent window. The mobile device may comprises a camera 64 that is located behind the second opening 62. The camera 64 may be realized by a camera semiconductor body.

Thus, the biometric sensor arrangement 10 may be realized on a backside of the mobile device. The heart rate sensor may be located on the backside of a smartphone. The second radiation source 12 is implemented as flash LED and is connected to a reversed diode realized by the first radiation source 11. The first radiation source 11 can be for example an IR, red or green emitting diode. Advantageously, the second radiation source 12 is located on the backside of the mobile telecommunication device 59 that may be mobile phone or a mobile smartphone.

Every opening in the backside of the housing 60 of a smartphone represents additional time and effort required for a research & development engineer in terms of designing, qualification testing and production. A reduction of openings 60, 61 and apertures to the inside of the mobile telecommunication device 59 reduces risk of failures, price of production and design efforts. Possible angular issues with the housing backside. Additionally, the smartphone keeps the look of simplicity when the number of openings 60, 61 in the housing 60 is small.

Also, the biometric sensor arrangement 10 advantageously reduces the cost for healthcare and achieves an improvement in performance.

The biometric sensor arrangement 10 uses the first radiation source 11 connected to the second radiation source 12 to emit a red, green or IR light for a heart rate measurement. The first radiation source 11 is a reversed diode and ESD diode to the second radiation source 12 implemented as flash LED. Advantageously, the opening of the flash LED on the backside of the phone can be designed for the emission signal.

In an alternative, not shown embodiment, the housing 60 comprises an additional opening for the receiving photodiode 17. The reflected radiation is detected through the additional opening. The second radiation source 12 emits through the opening 61. Thus, the photodiode 17 and the second radiation source 12 realizing a flash LED are optically isolated.

The first radiation source 11 may emit through the opening 61 or through the additional opening.

The optical crosstalk is improved compared to single emitter/receiver solutions. The optical path through the human body can be increased. Thus, a better signal-to-noise ratio is achieved, wherein the noise includes human movement.

Figure 3C:
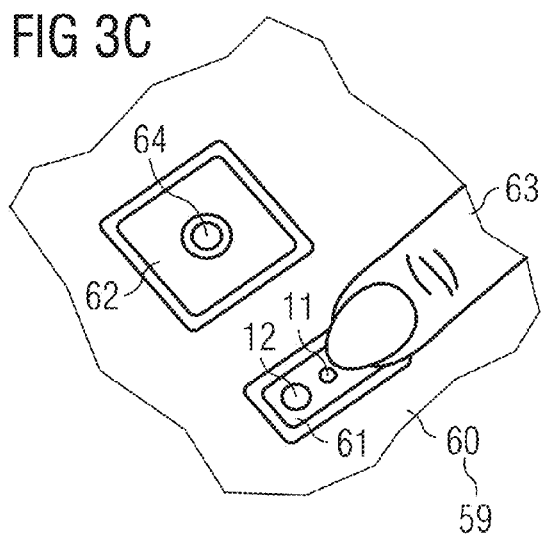
Figure 3D:
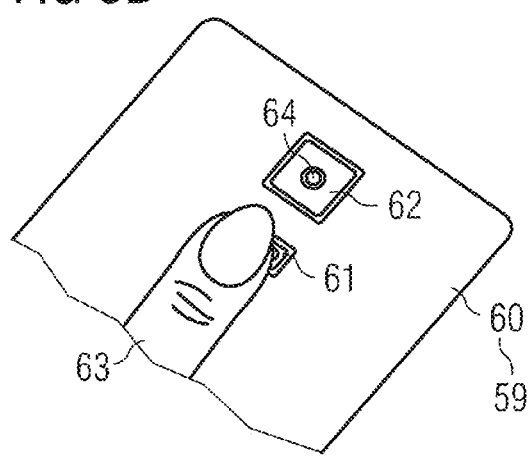

FIGS. 3C and 3D show the operation performed by the user of the biometric sensor arrangement 10 that can be realized as illustrated in one of the FIGS. 1A to 1G, 2A to 2D, 3A and 3B. A short light pulse emitted by the second radiation source 12 shows the user the place where the user has to put his finger 63, as illustrated by FIG. 3C. When the user has put his finger 63 on the right place, as shown in FIG. 3D, the biometric sensor arrangement 10 is able to perform the determination of the biometric signal SB and, thus, determines the pulse rate. Advantageously, the driver 13 is realized as a Flash LED Driver and can also be used as a heart rate sensor.

Figure 3E:
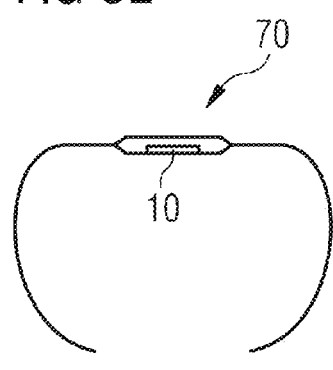

FIG. 3E shows an exemplary embodiment of a mobile device comprising the biometric sensor arrangement 10 that can be realized as illustrated in one of the above shown Figures. The mobile device is realized as a watch 70. The watch 70 comprises the biometric sensor arrangement 10. The watch 70 can also be called wrist watch. The biometric sensor arrangement 10 is located at a backside of the watch 70 such that the watch 70 is in direct contact to an arm of the user.

I claim:

1. A biometric sensor arrangement, comprising:
   a first radiation source,
   a second radiation source that is realized as flash light-emitting diode which is implemented as white light-emitting diode and is fabricated for conducting a high current that is higher than 500 mA,
   a driver coupled to the first and the second radiation source and configured to selectively operate the first and the second radiation source,
   a photosensor and
   a signal conditioning unit operable to provide a biometric signal,
   wherein the signal conditioning unit comprises a transimpedance amplifier and an analog-to-digital converter,
   wherein the transimpedance amplifier comprises an operational amplifier and a feedback resistor that couples a first input of the operational amplifier to an output of the operational amplifier
   wherein a terminal of the photosensor is connected to the first input of the operational amplifier,
   wherein a second input of the operational amplifier is connected to a reference potential terminal,
   wherein the first input of the operational amplifier is an inverting input, and the second input of the operational amplifier is a non-inverting input, and
   wherein the analog-to-digital converter is coupled to the output of the operational amplifier.

2. The biometric sensor arrangement according to claim 1, wherein the photosensor is configured to provide a photon signal as a function of radiation emitted by the first radiation source.

3. The biometric sensor arrangement according to claim 1, wherein the driver is configured to operate the first radiation source in a first operating phase and to operate the second radiation source in a second operating phase.

4. The biometric sensor arrangement according to claim 3, wherein the signal conditioning unit is configured to provide the biometric signal depending on a photon signal generated by the photosensor in the first operating phase and independent from the photon signal in the second operating phase.

5. The biometric sensor arrangement according to claim 3, wherein the driver is configured such that the second radiation source emits a flash in the second operating phase.

6. The biometric sensor arrangement according to claim 1, wherein the first radiation source is configured to emit radiation at a first wavelength and the second radiation source is configured to emit radiation at a second wavelength that is different from the first wavelength.

7. The biometric sensor arrangement according to claim 1, wherein the first and the second radiation source are realized as light-emitting diodes and form an anti-parallel circuit of diodes.

8. The biometric sensor arrangement according to claim 7, wherein the driver is implemented as a H-bridge that is configured to supply the first and the second radiation source.

9. The biometric sensor arrangement according to claim 7, wherein the driver comprises a current source, a further current source and a converter, and
   wherein the further current source couples a supply terminal to a first driver terminal, the current source couples an output of the converter to the first driver terminal and the first driver terminal is coupled to a terminal of the first radiation source and to a terminal of the second radiation source.

10. The biometric sensor arrangement according to claim 7, wherein the first radiation source is configured to protect the second radiation source in an event of an electrostatic discharge.

11. The biometric sensor arrangement according to claim 1, wherein the first and the second radiation source are arranged in vicinity and are configured to emit radiation through the same opening of a housing.

12. The biometric sensor arrangement according to claim 1, wherein the biometric sensor arrangement is configured to determine a heart rate of a user.

13. The biometric sensor arrangement according to claim 1, wherein the biometric sensor arrangement is configured to determine the concentration of at least one parameter in a skin of a user of a group consisting of melanin, water, fat, alcohol and oxygen.

14. A mobile device, comprising the biometric sensor arrangement according to claim 1, wherein the mobile device is realized as a mobile telecommunication device or a watch.

15. A method for generating a biometric signal, comprising:
   selectively operating a first and a second radiation source by a driver, wherein the second radiation source is implemented as a flash radiation source, providing a photon signal by a photosensor as a function of radiation emitted by the first radiation source and providing the biometric signal by a signal conditioning unit as a function of the photon signal, wherein providing the biometric signal comprises:

receiving the photon signal at a transimpedance amplifier of the signal conditioning unit, and generating a modified photon signal using an analog-to-digital converter of the signal conditioning unit, wherein the transimpedance amplifier comprises an operational amplifier and a feedback resistor that couples a first input of the operational amplifier to an output of the operational amplifier;

wherein a terminal of the photosensor is connected to the first input of the operational amplifier, and a second input of the operational amplifier is connected to a reference potential terminal, wherein the first input of the operational amplifier is an inverting input and the second input of the operational amplifier is a non-inverting input, and wherein the analog-to-digital converter is coupled to the output of the operational amplifier.

16. A biometric sensor arrangement, comprising:

a first radiation source, a second radiation source that is implemented as a flash radiation source, a driver coupled to the first and the second radiation source and configured to selectively operate the first and the second radiation source, a photosensor and a signal conditioning unit operable to provide a biometric signal, wherein the signal conditioning unit comprises a transimpedance amplifier and an analog-to-digital converter, wherein the transimpedance amplifier comprises an operational amplifier and a feedback resistor that couples a first input of the operational amplifier to an output of the operational amplifier wherein a terminal of the photosensor is connected to the first input of the operational amplifier, wherein a second input of the operational amplifier is connected to a reference potential terminal, wherein the first input of the operational amplifier is an inverting input, and the second input of the operational amplifier is a non-inverting input, wherein the analog-to-digital converter is coupled to the output of the operational amplifier wherein the first and the second radiation source are realized as light-emitting diodes and form an anti-parallel circuit of diodes, and wherein the first radiation source is configured to protect the second radiation source in an event of an electrostatic discharge.

* * * * *